United States Patent [19]

Hoos et al.

[11] Patent Number: 4,922,042

[45] Date of Patent: May 1, 1990

[54] PRODUCTION OF 1,2-DICHLOROETHANE

[75] Inventors: Keith M. Hoos, Cheshire, England; Jack Wolstenholme, Ontario, Canada

[73] Assignee: Imperial Chemical Industries PLC, London, England

[21] Appl. No.: 824,307

[22] Filed: Jan. 30, 1986

Related U.S. Application Data

[63] Continuation of Ser. No. 565,993, Dec. 27, 1983, abandoned.

[30] Foreign Application Priority Data

Dec. 24, 1982 [GB] United Kingdom ............... 8236851
Apr. 18, 1983 [GB] United Kingdom ............... 8310408

[51] Int. Cl.$^5$ .................... C07C 17/02; C07C 19/045
[52] U.S. Cl. .................................................... 570/247
[58] Field of Search ............... 570/255, 254, 251, 247

[56] References Cited

U.S. PATENT DOCUMENTS

| | | | |
|---|---|---|---|
| 2,099,231 | 11/1937 | Ruys et al. | 260/162 |
| 2,245,776 | 6/1941 | Groll et al. | 570/251 |
| 2,520,712 | 8/1950 | Cheney | 570/247 |
| 3,184,515 | 2/1962 | Penner et al. | 570/245 |
| 3,427,359 | 2/1969 | Rectenwald et al. | 570/245 |
| 3,481,995 | 12/1969 | Hartnett et al. | 260/662 |
| 4,069,170 | 1/1978 | Blake et al. | 570/243 |

FOREIGN PATENT DOCUMENTS

| | | | |
|---|---|---|---|
| 562010 | 8/1958 | Canada | 570/247 |
| 2733502 | 2/1979 | Fed. Rep. of Germany . | |
| 3106983 | 9/1982 | Fed. Rep. of Germany . | |
| 86387 | 12/1971 | German Democratic Rep. . | |
| 735587 | 5/1980 | U.S.S.R. | 570/247 |
| 1145912 | 3/1969 | United Kingdom . | |
| 2004272 | 3/1979 | United Kingdom . | |

Primary Examiner—J. E. Evans
Attorney, Agent, or Firm—Cushman, Darby & Cushman

[57] ABSTRACT

Process for the production of 1,2-dichloroethane by the reaction between ethylene and chlorine in the vapor phase in the presence of a catalyst comprising alumina, wherein the reaction is carried out using a fluidised bed comprising fluidisable, substantially spherical particles of alumina of surface area not exceeding 10 m$^2$g$^{-1}$ and especially in the range 0.2 to 6 m$^2$g$^{-1}$.

9 Claims, No Drawings

PRODUCTION OF 1,2-DICHLOROETHANE

This is a continuation of application Ser. No. 565,993, filed Dec. 27, 1983, which was abandoned upon the filling hereof.

This invention relates to a process for the production of 1,2-dichloroethane and more particularly to a vapour-phase process for the production of 1,2-dichloroethane.

The production of 1,2-dichloroethane by the liquid-phase chlorination of ethylene is well-known as a stage in the manufacture of vinyl chloride from ethylene. The liquid-phase chlorination of ethylene may be carried out, for example, in the presence of ferric chloride as catalyst using 1,2-dichloroethane itself as the reaction medium in a continuous process. Although this liquid-phase process can be carried out with high conversion of ethylene into 1,2-dichloroethane, the use of a liquid-phase process gives rise to problems in the purification and drying of the product. Thus, it is usually necessary to remove the catalyst from the product by washing with water, followed by washing with alkali to remove dissolved chlorine and hydrogen chloride and finally by drying.

The vapour-phase chlorination of ethylene to produce 1,2-dichloroethane has usually been regarded as a method of treating mixtures of gases containing a relatively low proportion of ethylene.

In UK Patent No. 1 230 604 there is described a process wherein an ethylene-containing stream derived from the effluent of an ethylene oxychlorination process is subjected to vapour-phase chlorination in the presence of activated alumina as catalyst. The proportion of ethylene in the effluent mixture subjected to chlorination was relatively low (about 3% by volume in the relevant example). Alumina was used in the form of a fixed bed of 6.4 mm spheres having a surface area of about 30 $m^2g^{-1}$.

Similarly, in German Specification 2733502 there is described a process in which residual gas from an oxychlorination process (containing from 2 to 12% by volume of ethylene) is treated with chlorine in the vapour phase in the presence of an alumina catalyst having a surface area of from 20 to 200 $m^2g^{-1}$; the example shows the use of a fixed bed of 6.4 mm spheres of alumina having a surface area of about 50 $m^2g^{-1}$.

However, vapour phase chlorination of ethylene using a fixed bed of catalyst particles is disadvantageous from a practical stand point in that temperature equalisation of the reaction mixture, and hence control of the reaction temperature, is difficult to achieve.

In East German Patent 86 387 there is described a process for the production of 1,2-dichloroethane in a fixed bed or fluidised bed reactor in which ethylene is chlorinated in the presence of nitrogen as diluent in the presence of a catalyst containing copper chloride and other metal chlorides on a support; one of the support materials described in gamma-alumina having a surface area from 150 to 350 $m^2g^{-1}$.

The use of a fluidised bed of alumina catalyst particles would be desirable from the point of view of achieving a more practical and economic process for the vapour phase chlorination of ethylene to 1,2-dichloroethane. Unfortunately, application of the prior art teaching to the problem of achieving such a fluidised bed process has in our experience resulted in a relatively low conversion of ethylene to 1,2-dichloroethane coupled with an unacceptably high proportion of unwanted by-products.

We have now found that it is nevertheless possible to carry out the reaction between ethylene and chlorine in a fluidised bed of a catalyst comprising substantially spherical alumina particles so as to achieve a very high conversion of ethylene into 1,2-dichloroethane together with a relatively low proportion of by-products (for example 'heavy' by-products such as 1,1,2-trichloroethane or 'light' by-products such as ethyl chloride).

According to the present invention there is provided a process for the production of 1,2-dichloroethane by the reaction between ethylene and chlorine in the vapour-phase in the presence of a catalyst comprising alumina, characterised in that the reaction is carried out using a fluidised bed comprising fluidisable, substantially spherical particles of alumina of surface area not exceeding 10 $m^2g^{-1}$.

The use of an alumina catalyst of a very low surface area (i.e. not exceeding 10 $m^2g^{-1}$) is a critical feature of our invention, since it unexpectedly and surprisingly results in very high conversion of ethylene to 1,2-dichloroethane with a low proportion of by-products—which as indicated above is not the result obtained when using the alumina catalysts of higher surface area taught by the prior art to achieve the vapour phase reaction of ethylene and chlorine to 1,2-dichloroethane.

The surface area of the said alumina is preferably in the range from 0.1 to 10 $m^2g^{-1}$, more preferably from 0.1 to 6 $m^2g^{-1}$, and especially from 0.2 to 6 $m^2g^{-1}$. A surface area of below 0.1 $m^2g^{-1}$ is not preferred as it tends to result in an excessively erosive reaction mixture. Alumina of surface area up to 6 $m^2g^{-1}$ is likely to be entirely of the alpha-alumina structure, while alumina of surface area in the range 6 to 10 $m^2g^{-1}$ is likely to be mostly of the alpha-alumina structure with up to a few percent of the gamma alumina structure.

Among suitable alumina materials are the 'catalyst carriers' of family type SAHT-96 and SAHT-99 (United Catalysts Inc) having surface areas of 1 to 5 $m^2g^{-1}$.

The alumina is preferably impregnated with a suitable alkaline-earth metal halide (preferably a chloride or a halide giving rise to the corresponding chloride under the reaction conditions) as this may improve still further the conversion to 1,2-dichloroethane and/or the lowering of the proportion of by-products; the impregnated alumina thus acts as a support as well as a catalyst. Impregnation may be conventionally effected by adding an aqueous solution of the halide to the alumina with stirring so as to produce a stiff homogeneous paste, followed by further stirring and heating to drive off the water. The preferred alkaline-earth metal is calcium. Suitable levels of impregnant are, for example, those corresponding to from 0.1 to 10 parts (preferably from 1 to 6 parts) by weight of the alkaline-earth metal per 100 parts by weight of alumina.

The chlorination process is preferably carried out at a temperature in the range 200° C. to 300° C., particularly in the range 200° C. to 260° C., in order to combine a conveniently high rate of reaction and the recovery of the heat of reaction in a useful form, e.g. by raising steam. The preferred residence time in the reaction zone will depend upon the reaction temperature, the composition of the feedstock, and the particular alumina catalyst employed, but in general residence times in the range 0.1 to 10 seconds are convenient.

Since the reaction between ethylene and chlorine to yield 1,2-dichloroethane is exothermic, the process is most conveniently carried out by balancing the flow-rates of the reactants, the proportion of any diluent and the extent of any cooling being applied in such a way that the desired reaction temperature is maintained.

Conventional quantities of ethylene and chlorine as used in prior art liquid and vapour-phase reactions may be employed in the process, i.e. normally stoichiometric quantities of ethylene and chlorine—although a slight molar excess of ethylene (with respect to the chlorine content), say a 5 to 15% molar excess, may conveniently be used.

The 1,2-dichloroethane produced may be separated from the gases leaving the reaction zone by condensation or other conventional techniques.

The invention is now illustrated by the following examples; the prefix C denotes a comparative example.

EXAMPLE 1

The catalyst used was 'SAHT-99-13' (United Catalysts Inc.), an alpha-alumina having substantially spherical particles of surface area 4 $m^2g^{-1}$. The alumina had been impregnated with calcium chloride to a level corresponding to 5 parts of calcium per 100 parts of alumina by weight. The catalyst was contained in a glass reactor tube of internal diameter 30 mm and was maintained in a fluidised state by passing the reactants upwardly through the bed. The heat of reaction was removed by passing air through a jacket surrounding the reactor tube. The reaction mixture contained 1.10 mole of ethylene (and 0.02 mole of oxygen) per mole of chlorine. The residence time in the reactor was 2 seconds and the temperature was 250° C. The reactor was allowed to operate under these conditions for 1 hour to eliminate transient effects, then for a further 1 hour during which the products from the reactor were collected and analysed by gas-liquid chromatography.

Conversion of the chlorine to chlorinated organic species was substantially quantitative and the conversion of ethylene substantially equivalent to that of chlorine. The product mix formed was 99.8% w/w 1,2-dichloroethane, 840 parts per million (ppm) w/w 'light' by-products (such as ethyl chloride), 540 ppm w/w 'heavy' by-products (such as 1,1,2-trichloroethane) and 200 ppm w/w trichloroacetaldehyde (chloral).

EXAMPLE C2

The catalyst used was 'Alumina Grade E-C' (Akzo Chemie), a gamma-alumina having substantially spherical particles of surface area 125 $m^2g^{-1}$. The alumina had been impregnated with calcium chloride to a level corresponding to 5 parts of calcium per 100 parts of alumina by weight. The procedure used was otherwise as described for Example 1.

Conversion of chlorine to chlorinated organic species was substantially quantitative and the conversion of ethylene substantially equivalent to that of chlorine. The product mix formed was 99.2% w/w 1,2-dichloroethane, 6390 ppm w/w 'light' by-products, 1060 ppm w/w 'heavy' by-products and 320 ppm w/w choral.

EXAMPLE C3

The catalyst used was 'Alumina Grade E-C' (Akzo Chemie) which had been calcined at 900° C. to reduce its surface area to 20 $m^2g^{-1}$. The alumina was impregnated with calcium chloride to a level corresponding to 5 parts of calcium chloride per 100 parts of alumina by weight. The procedure used was otherwise as described for Example 1.

Conversion of chlorine to chlorinated organic species was substantially quantitative and the conversion of ethylene substantially equivalent to that of chlorine. The product formed was 99.5% w/w 1,2-dichloroethane, 3610 ppm w/w 'light' by-products, 1450 ppm w/w 'heavy' by-products and 180 ppm w/w chloral.

The results of Example 1 to 3 are summarised in Table 1.

TABLE 1

| Example No. | Surface Area of Alumina Catalyst $m^2g^{-1}$ | Impregnated with calcium chloride? | Product Mix | | |
|---|---|---|---|---|---|
| | | | 1,2-dichloro-ethane % w/w | 'light' by-products ppm w/w | 'heavy' by-products ppm w/w | Chloral ppm w/w |
| 1 | 4 | Yes | 99.8 | 840 | 540 | 200 |
| C2 | 125 | Yes | 99.2 | 6390 | 1060 | 320 |
| C3 | 20 | Yes | 99.5 | 3610 | 1450 | 180 |

It is seen from Table 1 that operation of the process according to the invention in Example 1 gave the required product 1,2-dichloroethane in very high yield with a significantly lower proportion of unwanted by-products in comparison to the proportion of by-products obtained by operation of processes using exactly the same scale and construction of reactor but not according to the invention (Examples C2 and C3).

EXAMPLE 4

The catalyst used was 'SAHT-99-13' alumina which had been impregnated with calcium chloride to a level corresponding to 5 parts of calcium per 100 parts of alumina by weight. The catalyst was contained in a stainless steel reactor tube of internal diameter 50 mm and was maintained in a fluidised state by passing the reactants upwardly through the bed. The heat of reaction was removed by passing oil through a jacket surrounding the reactor tube. The reaction mixture contained 1.10 mole of ethylene (and 0.02 mole of oxygen) per mole of chlorine. The residence time in the reactor was 4 seconds and the temperature was 250° C. The reactor was allowed to operate under these conditions for 1 hour to eliminate transient effects, then for a further 1 hour during which the products from the reactor were collected and analysed by gas-liquid chromatography.

Conversion of the chlorine to chlorinated organic species was substantially quantitative and the conversion of ethylene substantially equivalent to that of chlorine. The product mix formed was 99.8% w/w 1,2-dichloroethane, 320 ppm w/w 'light' by-products, 1500 ppm w/w 'heavy' by-products and 40 ppm w/w chloral.

EXAMPLE 5

The catalyst was 'SAHT-99-13' alumina (surface area 4 $m^2g^{-1}$) and was used as received from the manufacturer (i.e. not impregnated with an alkaline-earth metal halide). The procedure was otherwise as described for Example 4.

Conversion of the chlorine to chlorinated organic species was substantially quantitative and the conversion of ethylene was substantially equivalent to that of chlorine. The product mix formed was 99.5% w/w 1,2-dichloroethane, 2542 ppm 'light' by-products, 1862 ppm w/w 'heavy' by-products and 176 ppm chloral.

EXAMPLE 6

The catalyst used was 'Sample Number 06596' (Norton Chemical Process Products Limited), an alpha-alumina having substantially spherical particles of surface area 0.25 $m^2g^{-1}$. The alumina was impregnated with calcium chloride to a level corresponding to 5 parts of calcium per 100 parts of alumina by weight. The procedure used was otherwise as described for Example 4.

Conversion of chlorine to chlorinated organic species was substantially quantitative and the conversion of ethylene substantially equivalent to that of chlorine. The product mix formed was 99.8% w/w 1,2-dichloroethane, 520 ppm w/w 'light' by-products, 1800 ppm w/w 'heavy' by-products and 66 ppm w/w chloral.

EXAMPLE C7

The catalyst used was 'Al3912P' (Harshaw Chemie BV), a gamma-alumina having substantially spherical particles of surface area 166 $m^2g^{-1}$. The alumina was impregnated with calcium chloride to a level corresponding to 5 parts of calcium per 100 parts of alumina by weight. The procedure used was otherwise as described for Example 4.

Conversion of chlorine to chlorinated organic species was substantially quantitative and the conversion of ethylene substantially equivalent to that of chlorine. The product mix formed was 98.6% w/w 1,2-dichloroethane, 8450 ppm w/w 'light' by-products, 4800 ppm w/w 'heavy' by-products and 450 ppm w/w chloral.

The results of Examples 4 to 7 are summarised in Table 2.

TABLE 2

| Example No. | Surface Area of Alumina Catalyst $m^2g^{-1}$ | Impregnated with calcium chloride? | Product Mix | | | |
|---|---|---|---|---|---|---|
| | | | 1,2-dichloroethane % w/w | 'light' by-products ppm w/w | 'heavy' by-products ppm w/w | Chloral ppm w/w |
| 4 | 4 | Yes | 99.8 | 320 | 1500 | 40 |
| 5 | 4 | No | 99.5 | 2542 | 1862 | 176 |
| 6 | 0.25 | Yes | 99.8 | 520 | 1800 | 66 |
| C7 | 166 | Yes | 98.6 | 8450 | 4800 | 450 |

It is seen from Table 2 that operation of the process according to the invention in Examples 4, 5 and 6 gave the required product in very high yield with a significantly lower proportion of unwanted by-products in comparison to the proportion of by-products obtained by operation of a process using exactly the same scale and construction of reactor but not according to the invention (Example C7).

We claim:

1. Process for the production of 1,2-dichloroethane by the reaction between ethylene and chlorine in the vapour phase in the presence of a catalyst consisting essentially of alumina or alumina impregnated with an alkaline earth metal halide, wherein the reaction is carried out using a fluidised bed consisting essentially of fluidisable, substantially spherical particles of said alumina or said alumina impregnated with alkaline earth metal halide, the surface area of said particles not exceeding 10 $m^2-g^{-1}$.

2. Process according to claim 1 wherein the alumina used has surface area in the range 0.2 to 6 $m^2g^{-1}$.

3. Process according to claim 1 wherein the alumina is impregnated with a alkaline-earth metal halide.

4. Process according to claim 3 wherein the alkaline-earth metal halide is a chloride or a halide giving rise to the corresponding chloride under the reaction conditions.

5. Process according to claim 3 wherein the alkaline-earth metal is calcium.

6. Process according to claim 3 wherein the level of impregnant corresponds to 0.1 to 10 parts by weight of the alkaline-earth metal per 100 parts by weight of alumina.

7. Process according to claim 6 wherein the level of impregnant corresponds to 1 to 6 parts by weight of the alkaline-earth metal per 100 parts by weight of alumina.

8. Process according to claim 1 wherein the chlorination reaction is carried out in the temperature range 200° to 300° C.

9. Process according to claim 1 wherein the residence time in the reaction zone is in the range 0.1 to 10 seconds.

* * * * *